United States Patent [19]

Takahashi

[11] 4,078,555
[45] Mar. 14, 1978

[54] CONTROL DEVICE FOR AN ENDOSCOPE

[76] Inventor: Nagashige Takahashi, No. 4-1, Nishi, Kokubunji, Tokyo, Japan

[21] Appl. No.: 643,651

[22] Filed: Dec. 23, 1975

[30] Foreign Application Priority Data

Dec. 26, 1974 Japan .............................. 50-3928[U]

[51] Int. Cl.² .............................................. A61B 1/00
[52] U.S. Cl. ......................................... 128/4; 128/6; 188/72.1; 188/72.7
[58] Field of Search ...................... 128/4-8, 128/DIG. 9; 188/71.2, 72.1, 72.3, 72.7

[56] References Cited

U.S. PATENT DOCUMENTS

| 3,256,875 | 5/1966 | Tsepelev et al. | 128/8 |
| 3,557,780 | 1/1971 | Sato | 128/4 |
| 3,788,303 | 1/1974 | Hall | 128/4 |

Primary Examiner—Robert W. Michell
Assistant Examiner—Henry S. Layton
Attorney, Agent, or Firm—Sughrue, Rothwell, Mion, Zinn and Macpeak

[57] ABSTRACT

An endoscope having control mechanism for permitting fine adjustment of the bending operation of a flexible tip. The flexible tip of an endoscope is controlled in its bending direction by rotating a knob at the opposite end of the endoscope. The knob is engageable by a braking clutch mechanism for stopping the rotation thereof and thereby fixing the position of the endoscope tip. A separate release mechanism is provided for temporarily disengaging the knob from the braking force of the clutch mechanism without requiring the release of the clutching mechanism to its disengaged state. The temporary release mechanism is operated by means of a button located on the knob thereby permitting easy operation while the physician or other operator is performing a viewing operation or the like.

5 Claims, 3 Drawing Figures

CONTROL DEVICE FOR AN ENDOSCOPE

BACKGROUND OF THE INVENTION

The present invention is in the field of endoscopes and, in particular, is directed to an endoscope which is easily adjusted after the flexible portion thereof is inserted within a cavity.

Endoscopes are well known in the art for examining internal human parts, such as mucous membrane, or, when combined with other instruments such as a forceps, for carrying out operations within a cavity of the human body. Typically an endoscope includes a flexible tube having a tip portion which may be controllably bent by a suitable manual operation carried out at the opposite end of the endoscope. The flexible tube with the tip thereon is inserted within a cavity and then the tip portion may be bent by manually operating a control at the opposite end of said endoscope to position the tip so that the desired mucous membrane part may be viewed. In such devices there is usually provided adequate braking means for holding the tip in the desired bent position. As will be literally apparent, in the absence of adequate braking means the tip would restore to its natural position which may not necessarily be the desired position for viewing a particular part of a mucous membrane.

If such braking operation is continuously applied, it would cause pain to those undergoing examination for obvious reasons. Therefore, it is also necessary and desirable to provide means for releasing the braking force when the operation is terminated so that the entire flexible tube including the tip thereof may assume a shape controlled entirely by the cavity. Thereafter, the endoscope can be easily removed from the cavity without pain. One such device which has been proposed for practical use in the field includes a clutching mechanism which is engaged to operate as a braking mechanism on the flexible tip and is disengaged to permit the flexible tip to assume a natural position resulting from the shape of the human cavity. However, fine adjustment of the tip is quite difficult with the latter apparatus because of the separation of the means for controlling the bending of the tip and the means for engaging the disengaging the clutch mechanism. For example, if one desires to make a fine adjustment of the tip direction when the endoscope is inserted and the clutch is engaged, one would be required to disengage the clutch and then alter the direction of the tip and subsequently engage the clutch. The disengagement of the clutch, however, will immediately permit the tip to freely assume its natural position. Consequently, fine adjustments become extremely difficult. To further complicate matters, the person operating the endoscope typically has only one free hand for operating the clutching and controlling mechanisms thereby increasing the difficulty of making a fine adjustment of the tip direction.

SUMMARY OF THE PRESENT INVENTION

According to the present invention, an endoscope is provided which does not suffer from the disadvantages mentioned above.

Therefore, it is an object of the present invention to provide an endoscope having a flexible tip portion which can controllably be adjusted by a simple manual operation acting upon controls at the end of said endoscope opposite from said tip.

In accordance with the present invention, an endoscope is provided having a flexible tube with a flexible tip for insertion in a cavity, such as a human cavity. Means are provided at the end of said endoscope opposite said tip for controlling the bending of said tip and a clutching mechanism is provided for selectively holding said tip in a fixed position and releasing the hold on said tip. An additional means is provided which releases the holding force on said controlling mechanism to permit the operator to adjust the direction of said tip by operating said controlling mechanism. The latter means is positioned so that it is actuated easily while holding said controlling mechanism in a single hand.

DETAILED DESCRIPTION OF THE PREFERRED EMBODIMENT

Figure 1:
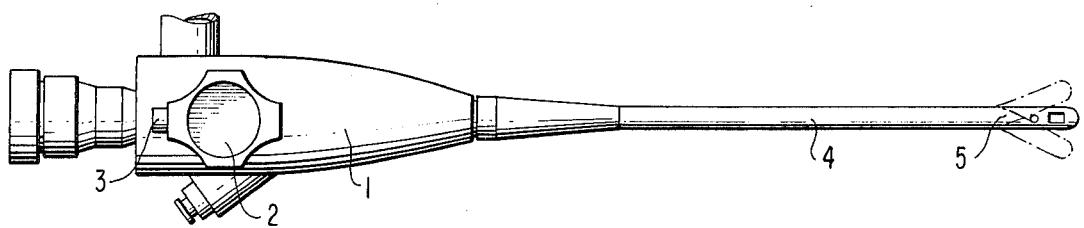
FIG. 1 is a side view schematically illustrating an endoscope provided with a device according to the present invention.

Referring to FIG. 1, there is shown a side view of an endoscope incorporating the novel features of the invention. The endoscope comprises an operating body 1 including an eye piece portion, a light carrying fiber bundle or a light guide, and an air feeding portion, all of which are well known in the art. Attached to the body 1 is a flexible tube having a flexible tip portion 5. The tip portion 5 may be arranged solely for viewing or may also include forceps or the like as is well known in the art. The bending of the tip portion 5 is controlled, as is typical by a two string apparatus connected between the tip and a rotating mechanism attached to the operating body 1. It is also known to provide a braking mechanism for preventing rotation of the aforementioned controlling mechanism thereby holding said flexible tip in a fixed bent direction. The novel features of the subject invention reside in the controlling and braking mechanism shown generally in FIG. 1 as a knob 2 having a push button 3 thereon. In general, the operation of the device of FIG. 1 is as follows.

The braking clutch is disengaged by movement of a lever (not shown) associated with the knob 2. The flexible tube is inserted into the cavity and thereafter the knob 2 is rotated to bend the tip 5 in the desired direction. When the desired direction is reached the aforementioned lever is operated to engage the braking clutch thereby preventing the knob from rotating and preventing the tip from altering its direction. When a fine adjustment is necessary the operator presses the button 3 on the knob 2 while holding the knob. The depression of button 3 releases the braking force of the aforementioned braking clutch permitting the operator to turn knob 2 so long as the button 3 is in the depressed condition. Consequently, fine adjustments of the bending direction may be accomplished. It should also be noted that the mechanism, to be described hereafter, is arranged so that the force exerted on the button 3 controls the ease with which the knob 2 may be rotated. Therefore, the operator has a great amount of control over the fine adjustment of the bending direction of the tip portion 5.

Figure 2:
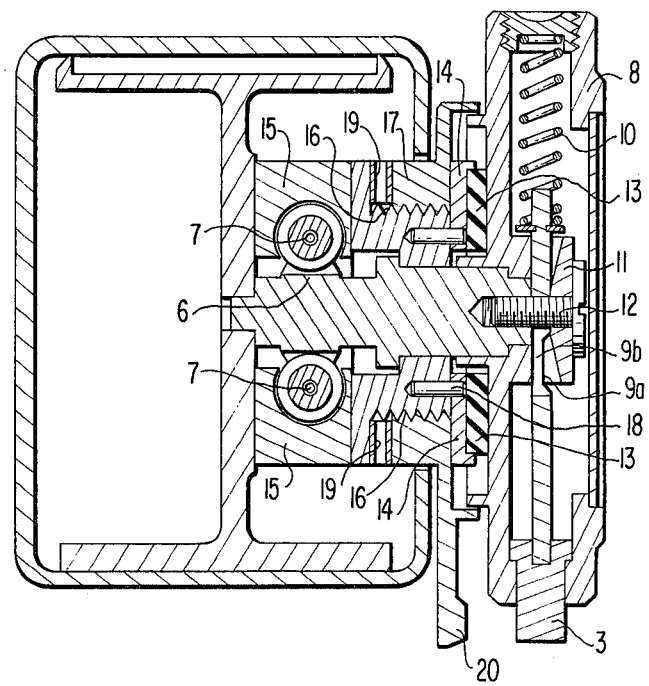
FIG. 2 is a longitudinal sectional side view showing a preferred embodiment of the device according to the invention.
Figure 3:
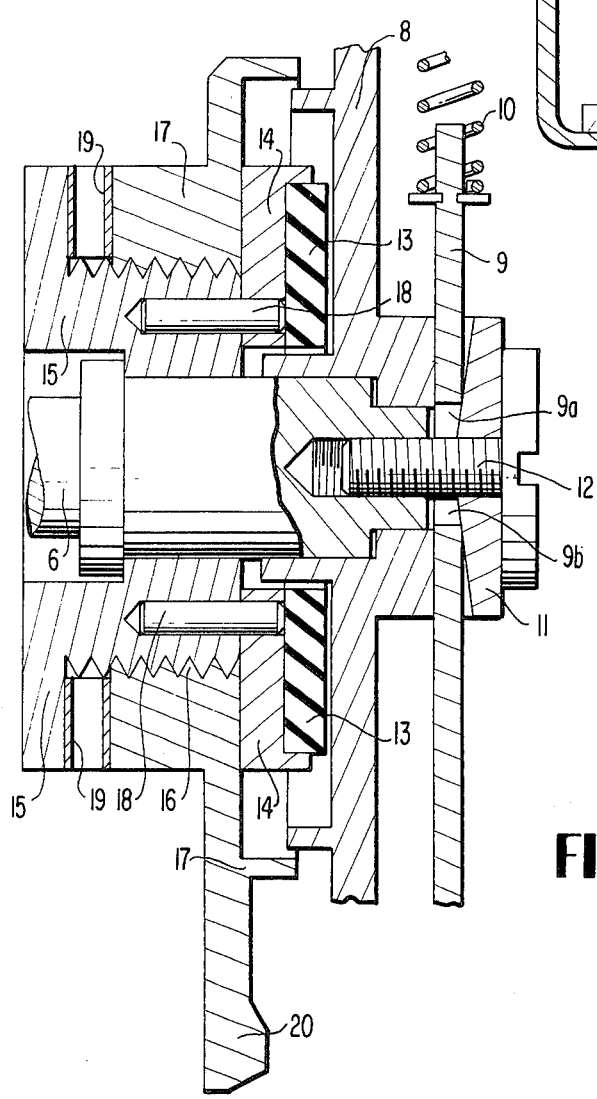
FIG. 3 is an enlarged longitudinal sectional side view of a principal part showing a state temporarily released in the device according to the invention.

A cross sectional view of the knob 2 attached to the operating portion 1 is illustrated in FIG. 2. An expanded view of certain portions shown in FIG. 2 is illustrated in FIG. 3. The mechanism is shown in FIG. 2 under the condition when the button 3 is not depressed, whereas the mechanism in FIG. 3 is shown under the condition when the button 3 is depressed.

Referring now collectively to FIGS. 2 and 3, the mechanism 2 is shown having a portion thereof fixed within the operating body 1. A pair of slide shafts 7 operate in a conventional manner to pull the strings (not shown) which control the bending direction of the tip. The strings are pulled as the shafts 7 rotate on operating shaft 6 by conventional linkage means such as a rack and pinion mechanism or the like. The main shaft 6, in turn, is rotated by the operating knob 8 which is attached thereto so as to be rotatably interlocked but axially movable with respect thereto over a small range. Thus, when the knob 8 rotates, the shafts 7 rotate to alter the relation between the strings and the flexible tip 20 to alter the direction of the flexible tip. If the device is left free the tip will resume its natural direction, thereby pulling on the strings and rotating the shaft 6 and the knob 8. Braking means for preventing the latter operation from occurring whenever the knob is manually released comprises an unmovable portion 15 fixed in the housing 1, a clutch operating ring 17 threadably engaged at 16 with the fixed member 15, a clutch plate 13 made of rubber or cork or the like for pressing against and braking the rotational movement of the knob 8, a holding member 14 fixed to said clutching plate 13 and movable axially in response to rotation of the clutch operating ring but fixed rotationally by means of pins 18 connected between the holding means 14 and the fixed member 15, and a spring means 19, such as a leaf spring, for imparting a force between fixed member 15 and clutch operating ring 17. The clutch operating ring is controlled by a lever 20 (shown only in FIG. 3) formed integrally therewith.

The clutching mechanism described operates as a braking force to prevent rotation of the knob when engaged therewith. Assume, for example, that the lever 20 is rotated to a position whereby the clutch operating ring has moved to the left in FIG. 2 so that the clutch plate 13 does not engage the knob 8 (contrary to that shown in FIG. 2). Under these conditions, the knob can be freely rotated, either manually or as a result of the tip changing from a fixed bent direction to its natural position. In order to provide the desired braking force, the lever 20 is rotated to cause the operating ring to rotate in a direction which moves the operating ring axially towards the right in FIG. 2. The latter movement is result of the threadable engagement of the operating ring and the fixed member 15. As the operating ring moves to the right it pushes holding member 14 and clutch plate 13 also to the right forcing clutch plate 13 into a strong frictional engagement with the knob 8. Pins 18 prevent rotation of the holding plate 14 and as a result the knob 8 cannot be rotated.

The apparatus for selectively and controllably releasing the braking force of the clutching mechanism to thereby permit fine adjustments of the flexible tip comprises a release plate 9 and biasing spring 10 within the knob 8, a button 3 attached to the release plate for pushing said plate against the force of spring 10, a screw 12, and a tightening member 11. As can be seen in the figures, the screw 12 is threadably engaged with the shaft 6 through an opening in the tightening member 11 and a slot in the release plate 9. The release plate 9 is biased in a downward direction (as shown in the figures) by means of the biasing spring 10. The release plate 9 also includes a thinner portion 9a which, when the release plate is in its fully downward position, is just below the shaft of screw 12. The tightening member 11 has its fixed cross section near the opening through which the shaft of screw 12 passes. The screw 12 is adjusted to the position shown in FIG. 2 when the plate 9 is in the down position. The adjustment is made so that the plate 9 may be moved upwardly against the biasing force of the spring when the button 3 is depressed.

Referring now specifically to FIG. 3, wherein the plate 9 is shown in the position it assumes when the button is depressed, it can be seen that the thin portion 9a of the plate 9 moves to a position in substantial axial alignment with the screw 12, the tightening member 11, and the shaft 6. As a result thereof, and further as a result of the shape of the tightening member 11, which as illustrated is wider towards the opening through which the screw shaft passes, a space is created between the plate 9 and the tightening member 11. Consequently, the axial pressure on the knob 8 which is applied by the screw 12, is slightly released permitting the knob 8 to become disengaged from the clutch plate 13. This further permits the knob to be rotated, but only so long as the button 3 is depressed. It thus becomes apparent that the operator can simply make a fine tuning, i.e., adjustment, of the tip direction without restoring the tip first to its completely free state by simply depressing button 3 with one finger while holding slightly rotating the knob 8 with remaining parts of the same hand.

According to the device of the present invention, which includes a member for temporarily releasing braking on the flexure operating knob, the holding action of the braking mechanism may be released permitting fine adjustment of the direction of the flexible tip after the tip portion has been previously braked and held. The temporary release operation is integral with the bending operation, such as the gripping and turning of an operating knob, so that manual operation may very easily be accomplished in a human engineering mode while an examiner is concentrating on his observation or the like. Further, in accordance with the present invention, the aforementioned temporary release may be accomplished by the movement of the operating knob in the direction of release relative to the direction where braking action is exerted without acting upon the braking side of the clutch plate mechanism. Therefore, the device of the present invention may easily be incorporated into conventional endoscope operating mechanisms. When a forceps is inserted to an endoscope, the operating knob becomes heavy in its operation, resulting in an extreme difficulty of operation under braking conditions, whereas according to the device of the present invention, braking may easily be released, with the result that an essential function of the forceps, such as aiming at the target, may also be enhanced.

Further, according to the device of the present invention, the relationship between the flexure operating knob and the release member is such that both can be easily controlled simultaneously. In addition, it will of course be noted that suitable means such as a lever mechanism associated with the operating knob may be employed as the release member in place of the button mechanism.

What is claimed is:

1. In an endoscope of the type having a flexible member with a tip portion controllable in its bending direction by a control knob at the manual operation end of said endoscope and a braking means, selectively movable to an engagement position and a disengagement position relative to said knob, for braking and releasing said knob and said tip portion, the improvement comprising release means, having a manually actuable part sufficiently close to said knob to permit manual operation of both by one hand simultaneously, for releasing said knob and said tip from the braking force of said braking means even when said braking means is in the engagement position wherein said braking means comprises a clutch plate, and means operative to press said clutch plate in engagement with a part that is rotationally fixed with said knob, said release means comprising,
   (a) first adjustable means for adjusting the engaging force between said clutch plate and said part when said clutch plate is in the engagement position and said release means is not actuated, and
   (b) release plate positioned adjacent said first adjustable means and movable relative thereto for reducing said engaging force when moved from a first position to a second position.

2. In an endoscope of the type having a flexible member with a tip portion controllable in its bending direction by a control knob at the manual operation end of said endoscope and a braking means, selectively movable to an engagement position and a disengagement position relative to said knob, for braking and releasing said knob and said tip portion, the improvement comprising release means, having a manually actuable part sufficiently close to said knob to permit manual operation of both by one hand simultaneously, for releasing said knob and said tip from the braking force of said braking means even when said braking means is in the engagement position wherein said release means comprises, a screw having a head and a shaft, a tightening member positioned on said shaft, said tightening member being relatively thicker towards the center thereof, a release plate positioned within said knob and movable longitudinally in the plane of rotation of said knob, said plate having a slot therein thru which said screw shaft passes, said slot being aligned with the axis of movement of said plate, said plate further having a portion thereof substantially thinner than the normal thickness of said plate, spring means in said knob biasing said plate in a first position wherein a thick part of said plate abuts the thick part of said tightening member, the opposite side of said plate abutting said knob, said screw shaft being threadably engaged with an axially fixed member in said endoscope to permit adjustment of said knob in the engagement and disengagement direction with said braking means, and wherein said manually actuable part of said release means is attached to said release plate so that the manual actuation of said part moves said release plate against the force of said bias spring to cause the thin part thereof to abut the thick part of said tightening ring, thereby releasing the pressure directed by said screw, said ring and said plate against said knob.

3. The apparatus of claim 2 wherein said manually actuable part comprises a push button attached at one end thereof to said plate and having at least the other end thereof extending outside of said knob.

4. The apparatus of claim 3 wherein the manually actuable part of said release means is a button on said knob.

5. A flexure controlling device for an endoscope of the type in which the bending of a flexure portion at the tip of a flexible tube of the endoscope to be inserted into a body cavity is controlled by pulling a string which is controlled by a control member the movement of which is engaged by a clutch member, characterized in that said control member is movable in the directions towards and away from said clutch member, and in that a release member is provided in said control member, said release member being adapted to temporarily disengage said control member from engagement with said clutch member, to thereby make a temporary movement of said control member away from said clutch member possible.

* * * * *